(12) United States Patent
Takasawa

(10) Patent No.: US 7,120,229 B2
(45) Date of Patent: Oct. 10, 2006

(54) RADIOGRAPHIC IMAGING CONTROL APPARATUS AND METHOD

(75) Inventor: Toru Takasawa, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 4 days.

(21) Appl. No.: 11/044,759

(22) Filed: Jan. 26, 2005

(65) Prior Publication Data

US 2005/0169425 A1    Aug. 4, 2005

(30) Foreign Application Priority Data

Jan. 30, 2004    (JP)    ............................ 2004-024588

(51) Int. Cl.
*H05G 1/64*    (2006.01)
(52) U.S. Cl. .................. 378/98.2; 378/62; 378/108
(58) Field of Classification Search .............. 378/62, 378/96–98, 98.2, 98.12, 108; 250/370.08, 250/370.09
See application file for complete search history.

(56) References Cited

U.S. PATENT DOCUMENTS 6,795,526 B1 *    9/2004    Kump et al. ................ 378/116

FOREIGN PATENT DOCUMENTS

JP    2001-149359 A    6/2001

* cited by examiner

*Primary Examiner*—Courtney Thomas
(74) *Attorney, Agent, or Firm*—Morgan & Finnegan, LLP

(57) ABSTRACT

An X-ray imaging control apparatus acquires radiographic data obtained from an X-ray imaging apparatus which controls an X-ray dose upon X-ray imaging by detecting the X-ray dose in one or a plurality of detection regions, and displays a radiographic image on the basis of the acquired radiographic data. At this time, detection region information indicating the position and range of each detection region used in the X-ray imaging apparatus upon generating the radiographic data is acquired. Based on this detection region information, an image indicating each detection region is superimposed on the displayed radiographic image.

13 Claims, 16 Drawing Sheets

FIG. 7A

AEC REGION TABLE
[ STANDING POSITION SENSOR ]     10

| AEC No. | START POINT POSITION | SIZE |
|---|---|---|
| AEC1 | 844,518 | 200,300 |
| AEC2 | 1657,518 | 200,300 |
| AEC3 | 1244,1244 | 200,300 |
| AEC4 | 0.0 | 0.0 |
| AEC5 | 0.0 | 0.0 |

IMAGING METHOD-DEPENDENT AEC REGION TABLE

[ CHEST PA ]
(IMAGING METHOD ID=CHEST001)

11

| AEC No. | On/Off |
|---|---|
| AEC1 | On |
| AEC2 | On |
| AEC3 | Off |
| AEC4 | Off |
| AEC5 | Off |

231

[ ABDOMEN AP ]
(IMAGING METHOD ID=ABDMN001)

| AEC No. | On/Off |
|---|---|
| AEC1 | Off |
| AEC2 | Off |
| AEC3 | On |
| AEC4 | Off |
| AEC5 | Off |

232

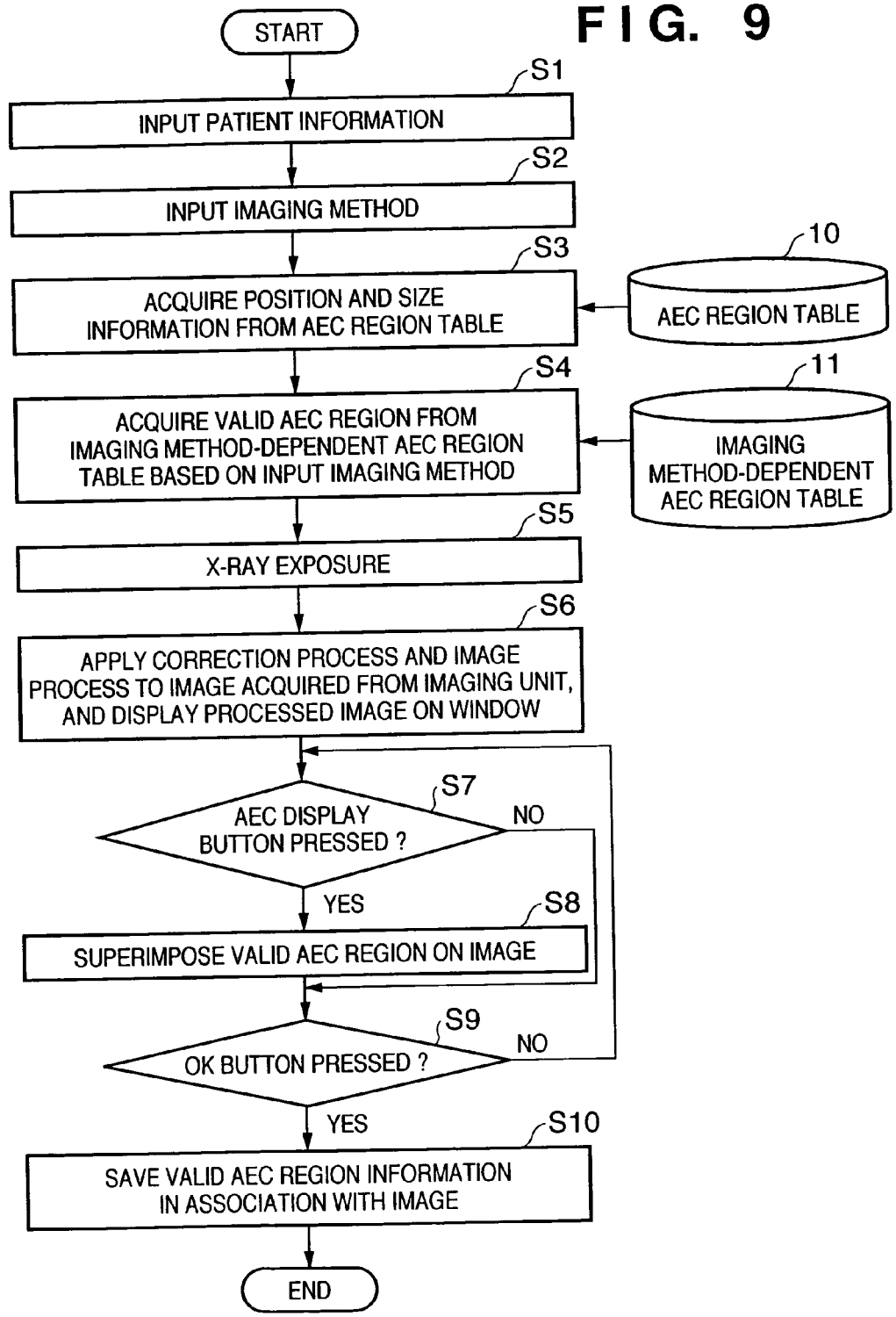

FIG. 10A

PATIENT INFORMATION AND IMAGING METHOD INFORMATION TRANSFERRED FROM HIS/RIS BEFORE IMAGING

| Cano Taro,12345,M,1965.04.16,..... | |
|---|---|
| CHEST | PA,CHEST001,AEC1=1,AEC2=1,AEC3=0,AEC4=0,AEC5=0,KV=130,....,IP=... |
| ABDOMEN | AP,ABDMN001,AEC1=0,AEC2=0,AEC3=1,AEC4=0,AEC5=0,KV=130,....,IP=... |

FIG. 10B

EXECUTION INFORMATION TRANSFERRED FROM GENERATOR AFTER IMAGING

| ABDOMEN | AP,ABDMN001,AEC1=0,AEC2=0,AEC3=1,AEC4=0,AEC5=0,KV=130 |
|---|---|

RADIOGRAPHIC IMAGING CONTROL APPARATUS AND METHOD

FIELD OF THE INVENTION

The present invention relates to a radiographic imaging apparatus which obtains a radiographic image by automatically controlling the dose of radiation on a patient.

BACKGROUND OF THE INVENTION

As an X-ray imaging apparatus that aims at medical diagnosis, an X-ray photography system using an X-ray detector that includes an intensifying screen and film. In recent years, a digital X-ray imaging system that generates an image by digitally detecting X-rays has prevailed in place of such X-ray photography system. Typical one of digital X-ray imaging apparatuses acquires an X-ray image using a flat panel sensor as a detection device. In this apparatus, a solid-state imaging element which has sensitivity to X-rays and converts and outputs an electrical signal corresponding to the detected X-ray intensity, or a unit which combines a phosphor that absorbs X-ray energy and emits fluorescence accordingly, and a photoelectric conversion element that has sensitivity to visible light and converts it into an electrical signal corresponding to light intensity is used, and an analog signal from such element is A/D-converted into digital data, thus acquiring an X-ray image.

Such digital X-ray imaging apparatus comprises an examination module including a detection device which detects the quantity of electricity according to an X-ray transmitted dose, and converts it into a digital quantity, and a controller which controls this examination module and an X-ray generator. In general, a so-called X-ray imaging system is formed by combining this digital X-ray imaging apparatus, a monitor or printer that displays (outputs) a radiographic image, and an X-ray generator. In such digital X-ray imaging system, digital image data from the examination module is sent to a controller and undergoes various image processes, and an X-ray digital image to be diagnosed by a doctor is acquired using the processed image data. The generated digital image is output onto a film via a printer as needed or is displayed on a monitor to make a diagnosis after it is sent to a storage.

A general digital imaging apparatus will be described below with reference to FIG. 15. Referring to FIG. 15, reference numeral 1000 denotes an X-ray tube; 1001, an X-ray generator controller; 1002, an X-ray generator console as a console of the X-ray generator controller 1001; 1003, an imaging unit; 1004, an AEC device; 1005, an X-ray detector; 1007, an imaging controller in the X-ray imaging system; 1008, a display unit that displays an X-ray image; and 109, a patient. Note that the X-ray tube 1000, X-ray generator controller 1001, and console 1002 form an X-ray generator.

When a radiation generation signal transmitted from the controller 1007 of the X-ray imaging system is ON, the X-ray generator controller 1001 controls the X-ray tube 1000 to generate radiation. The radiation generated by the X-ray tube 1000 is transmitted through the patient 109 as an object to be examined, and reaches the imaging unit 1003. At this time, the radiation is scattered and absorbed inside the body of the patient. Since only primary radiation that goes straight through the patient can be used in imaging, scattered radiation is not necessary for the X-ray detector 1005. Hence, a grid (not shown) is normally provided to remove unnecessary scattered radiation to improve the contrast of a radiographic image.

The grid (not shown) is a plate formed by cutting a lamination obtained by alternately laminating lead plates and aluminum plates, in a direction perpendicular to the layer direction, and removes unnecessary scattered radiation generated from the patient 109 by arranging such plates which are juxtaposed nearly parallelly in a direction that agrees with the primary radiation propagation direction. A radiographic image of the grid is recorded by the X-ray detector 1005 to be superimposed on a radiographic image which is transmitted through the patient 109. In this case, the grid image does not pose any problem in diagnosis by appropriately selecting the spatial frequency of the grid.

The patient 109 scatters and absorbs radiation, but the degrees of scattering and absorption depend on the structure of the patient 109. Simply put, a patient with a large body thickness has high degrees of scattering and absorption, but a patent with a small body thickness has low degrees of scattering and absorption. Even when the body thickness remains the same, the degrees of scattering and absorption change depending on a muscular or fatty body type. Furthermore, the degrees of scattering and absorption change depending on a portion to be radiographed. For this reason, it is difficult to accurately estimate primary radiation dose transmitted through the patient 109 before imaging.

Hence, the X-ray imaging apparatus normally has an AEC (Automatic Exposure Control) device (see Japanese Patent Laid-Open No. 2001-149359). The AEC device is also called a phototimer in Japan. The AEC device is provided to minimize exposure on a human body and to appropriately generate a radiation dose required for the X-ray imaging apparatus. In the imaging unit 1003, the grid (not shown), AEC device 1004, and X-ray detector 1005 are laid out in turn from the entrance side of radiation. The AEC device 1004 detects some rays of the radiation which has been transmitted through the patient 109 and grid in real time, and transmits them as an AEC signal to the X-ray generator controller 1001. When the integrated value of the AEC signal has exceeded a threshold value, the X-ray generator controller 1001 turns off the radiation generation signal to stop generation of radiation. In this manner, the AEC device 1004 appropriately controls the radiation dose upon X-ray imaging.

FIG. 16 is a view for explaining the positional relationship between the X-ray detector 1005 and AEC device 1004. The X-ray detector 1005 is formed by arranging 2688×2688 160-$\mu m^2$ square pixels in a matrix. In this case, an AEC device 1004 having three regions is attached. Imaging is made by selectively using one or a plurality of the three AEC regions in accordance with a portion to be radiographed as needed. When a region of interest is located at the center (e.g., abdomen or head), the central region C is selected; in chest imaging having both lungs as regions of interest, the upper right and upper left regions B and A are selected. After the AEC region (or regions) is selected, positioning is made to irradiate the region of interest of the patient with required X-rays. For example, in chest PA imaging, the patent stands with his or her back to the X-ray tube 1000 and with his or her chin on the upper end of the imaging unit 1003. Also, the patient raises shoulders by lightly turning arms behind him or her so as to allow easy observation of the lung fields. After positioning of the patient is normally done, imaging conditions such as a tube voltage, tube current, and the like and the selected region (or regions) of the AEC device are confirmed to appropriately set the dose of the region of interest, thus making an imaging process.

Note that the AEC device 1004 takes various attentions so as not to influence the image quality and exposed dose while sufficiently effecting its function. The AEC device 1004 covers very small areas of the X-ray detector 1005, e.g., the upper right and left portions corresponding to the two lung portions and the central portion, so as not to increase the exposed dose in the AEC device. Also, the AEC device is designed not to influence X-ray imaging. By detecting the radiation doses of partial regions of characteristic lung fields, an appropriate density is set for the entire lung fields in the obtained radiographic image. Furthermore, when the AEC device 1004 is superimposed on a patient image, it becomes an artifact. Hence, the AEC device 1004 is designed to shield nearly no X-rays. For example, the AEC device 1004 is a flat air bath, the outer periphery of which is made up of a material that does not shield radiation as much as possible. By collecting slight charges ionized in this air bath due to radiation, the radiation dose is detected. Or the AEC device 1004 is a thin fluorescent screen, which detects fluorescence generated by radiation using a photo-intensifier. Furthermore, an incoming X-ray dose may be integrated using a portion of the X-ray detector 1005 to shield X-rays radiated from the X-ray tube 1000.

The X-ray detector 1005 detects a radiographic image obtained using an appropriate radiation dose, and the controller 1007 of the X-ray imaging system applies various image correction processes and image processes to obtain a diagnosis image, which is set before diagnosis.

However, in the aforementioned X-ray imaging apparatus, when the AEC regions (A, B, and C) are not appropriately selected, or when positioning of the patient is incorrect, AEC does not function normally and results in an insufficient dose, and the image graininess drops, thus adversely influencing diagnosis. In such case, the operator must select correct AEC regions again or must re-make positioning of the patient to perform an imaging process again. Conventionally, since the operator cannot immediately recognize any selection errors of AEC regions or any deviations of AEC regions from the regions of interest, it is difficult to perform an imaging process under appropriate X-ray dose control using AEC.

Especially, in case of a side imaging process of a body, individual differences are large, and it is difficult to determine the position of interest of a spine from outside due to a different body thickness. Hence, even when the imaging process is repeated, appropriate X-ray dose control cannot be done based on correct AEC.

SUMMARY OF THE INVENTION

The present invention has been made in consideration of the above situation, and has as its object to clearly specify the positions of respective detection regions of an automatic exposure control (AEC) device on a radiographic image, and to allow an easy imaging process under appropriate radiation dose control using AEC.

According to one aspect of the present invention, there is provided a radiographic imaging control apparatus comprising: a first acquisition unit configured to acquire radiographic data obtained from a radiographic imaging apparatus which controls a radiation dose upon radiographic imaging by detecting a radiation dose in one or a plurality of detection regions; a first display unit configured to disaplay a radiographic image on the basis of the radiographic data acquired by the first acquisition unit; a second acquisition unit configured to acquire detection region information indicating a position and range of each detection region used in the radiographic imaging apparatus upon generating the radiographic data; and a second display unit configured to superimpose an image indicating each detection region on the radiographic image displayed by the first display unit on the basis of the detection region information acquired by the second acquisition unit.

Furthermore, according to another aspect of the present invention, there is provided an X-ray imaging control method comprising: a first acquisition step of acquiring radiographic data obtained from an X-ray imaging apparatus which controls an X-ray dose upon X-ray imaging by detecting an X-ray dose in one or a plurality of detection regions; a first display step of displaying a radiographic image on the basis of the radiographic data acquired in the first acquisition step; a second acquisition step of acquiring detection region information indicating a position and range of each detection region used in the X-ray imaging apparatus upon generating the radiographic data; and a second display step of superimposing an image indicating each detection region on the radiographic image displayed in the first display step on the basis of the detection region information acquired in the second acquisition step.

Furthermore, according to another aspect of the present invention, there is provided a n X-ray imaging system including an X-ray imaging unit and a control unit for controlling the X-ray imaging unit, comprising: first acquisition means for acquiring radiographic data obtained from the X-ray imaging unit which controls an X-ray dose upon X-ray imaging by detecting an X-ray dose in one or a plurality of detection regions; transmission means for transmitting the radiographic data to the control unit; first display means for displaying a radiographic image on the basis of the radiographic data transmitted from the transmission means; second acquisition means for acquiring detection region information indicating a position and range of each detection region used in the X-ray imaging apparatus upon generating the radiographic data; and second display means for superimposing an image indicating each detection region on the radiographic image displayed by the first display means on the basis of the detection region information acquired by the second acquisition means.

According to the present invention, since the positions of respective detection regions of an automatic exposure control (AEC) device on a radiographic image can be clearly specified, an imaging process can be easily made under appropriate radiation dose control using AEC.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 7A shows a data configuration example of an AEC region table, and FIG. 7B shows data configuration examples of imaging method-dependent AEC region tables;

FIG. 9 is a flowchart for explaining the processing sequence of an imaging system controller according to the first embodiment;

FIGS. 10A and 10B show a data configuration example of patient information and imaging portion information in imaging request information acquired from HIS and RIS, and a data configuration example of execution information acquired from a generator;

DETAILED DESCRIPTION OF THE PREFERRED EMBODIMENTS

Preferred embodiments of the present invention will now be described in detail in accordance with the accompanying drawings.

First Embodiment

Figure 1:
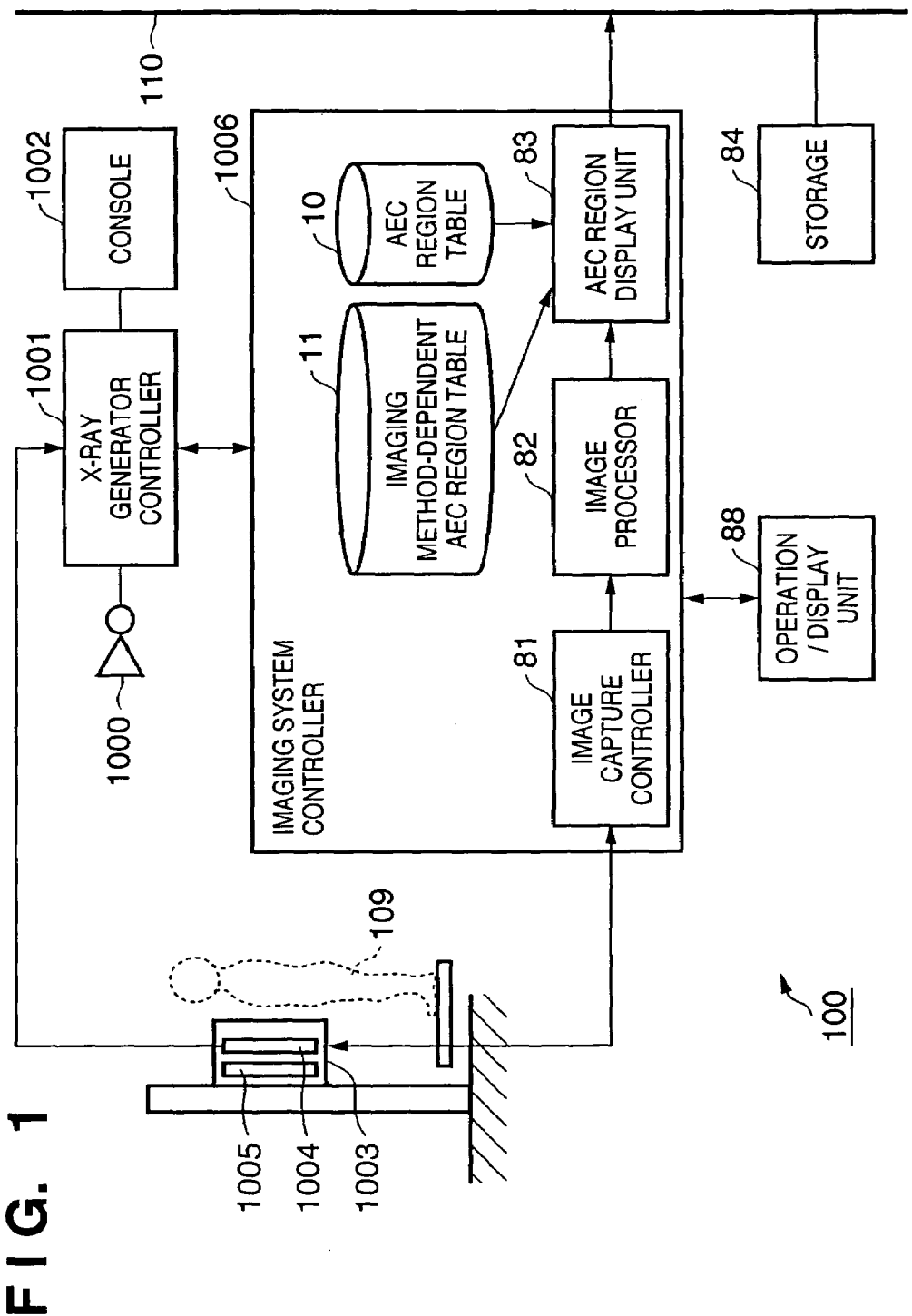
FIG. 1 is a block diagram for explaining the arrangement of an X-ray imaging system according to an embodiment of the present invention.
Figure 15:
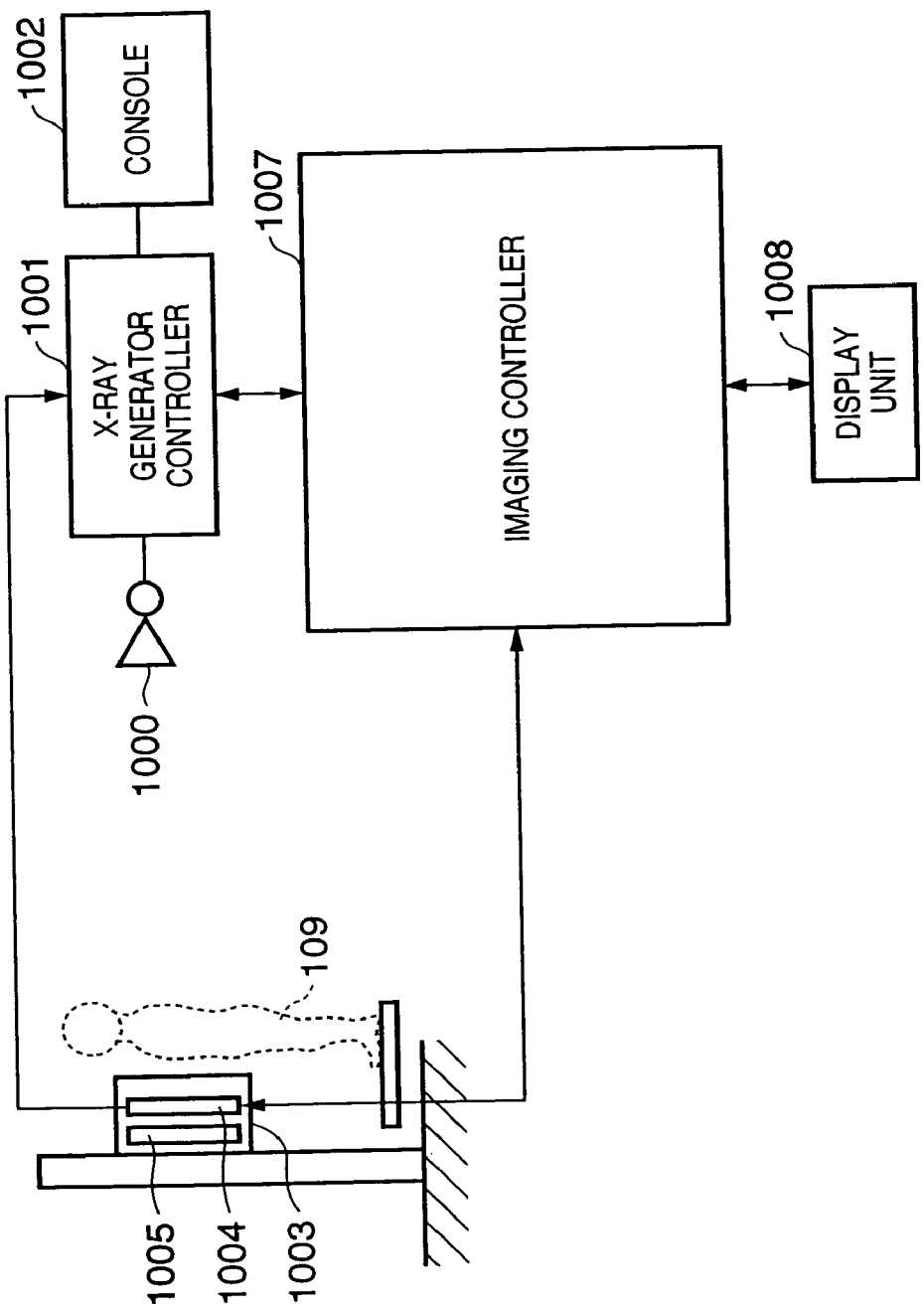
FIG. 15 is a block diagram showing the arrangement of a general X-ray imaging system.

FIG. 1 is a block diagram showing the arrangement of an X-ray imaging system 100 according to the first embodiment. The X-ray imaging system 100 comprises an X-ray tube 1000, X-ray generator controller 1001, X-ray generator console 1002, imaging unit 1003, and the like, which have been explained using FIG. 15. An imaging system controller 1006 processes a digital image signal obtained from the imaging unit 1003, and makes various kinds of control for an X-ray generator.

The X-ray generator controller 1001 controls application of a high voltage to the X-ray tube 1000 in accordance with the imaging conditions such as a tube current, tube voltage, irradiation time, and the like, which are sent from the X-ray generator console 1002 and imaging system controller 1006, and an AEC signal from an AEC device 1004.

The imaging unit 1003 includes an X-ray detector 1005 which detects X-rays emitted by the X-ray tube 1000 and obtains a digital image, the AEC device 1004 which is used to minimize exposure on a human body and to appropriately obtain a radiation dose required for the imaging apparatus, a grid (not shown), and an A/D converter which outputs the output from the X-ray detector as a digital image signal. The X-ray detector 1005 is a flat panel sensor (flat panel detector (FPD)) that forms an image of an X-ray two-dimensional distribution obtained when X-rays generated by the X-ray generator are transmitted through a human body, and includes a scintillator which converts X-rays into light, and a solid-state imaging element which converts the light output from the scintillator into an electrical signal according to its light intensity. As the X-ray detector 1005, a solid-state imaging element which has sensitivity to X-rays, and converts and outputs an electrical signal according to the intensity of detected X-rays may be used. Of X-rays that come from the X-ray tube 1000, enter the imaging unit 1003 and are transmitted through a patient 109, scattered X-rays generated by the patient 109 are removed by the grid. The X-rays transmitted through the grid are converted by the scintillator into light, and the solid-state imaging element generates an electrical signal corresponding to the light intensity. The electrical signal is converted into a digital signal by the A/D converter, thus obtaining a digital X-ray image.

The AEC device 1004 is arranged between the grid and X-ray detector 1005, detects some rays of radiation transmitted through the grid in real time, and transfers an AEC signal to the X-ray generator controller 1001. When the integrated value of the transferred AEC signal has exceeded a threshold value, the X-ray generator controller 1001 turns off a radiation generation signal to stop generation of radiation from the X-ray tube 1000. In this manner, the radiation dose is appropriately controlled using the AEC device 1004.

The imaging system controller 1006 captures a digital image signal transferred from the imaging unit 1003 via an image capture controller 81, and applies predetermined image processes in an image processor 82. The processed X-ray image is displayed by an operation/display unit 88, is transferred to and stored in a storage 84 via a network 110, or is output via a printer (not shown). An AEC region display unit 83 composites and displays an AEC region (or regions) used in control of the radiation dose on a radiographic image of the patient on the operation/display unit 88. Note that position information of AEC regions may be added upon storing an X-ray image in the storage 84.

The operation/display unit 88 includes an operation unit used to make various operations and AEC setups in the X-ray imaging system 100, and a monitor used to display a radiographic image, messages, various setting states, and the like. The operation/display unit 88 may include a liquid crystal panel, touch sensor, and mouse, as is known to those who are skilled in the art. An AEC setting value input from the operation/display unit 88 is stored in a memory as an AEC region table 10 or imaging method-dependent AEC region table 11.

Figure 2:
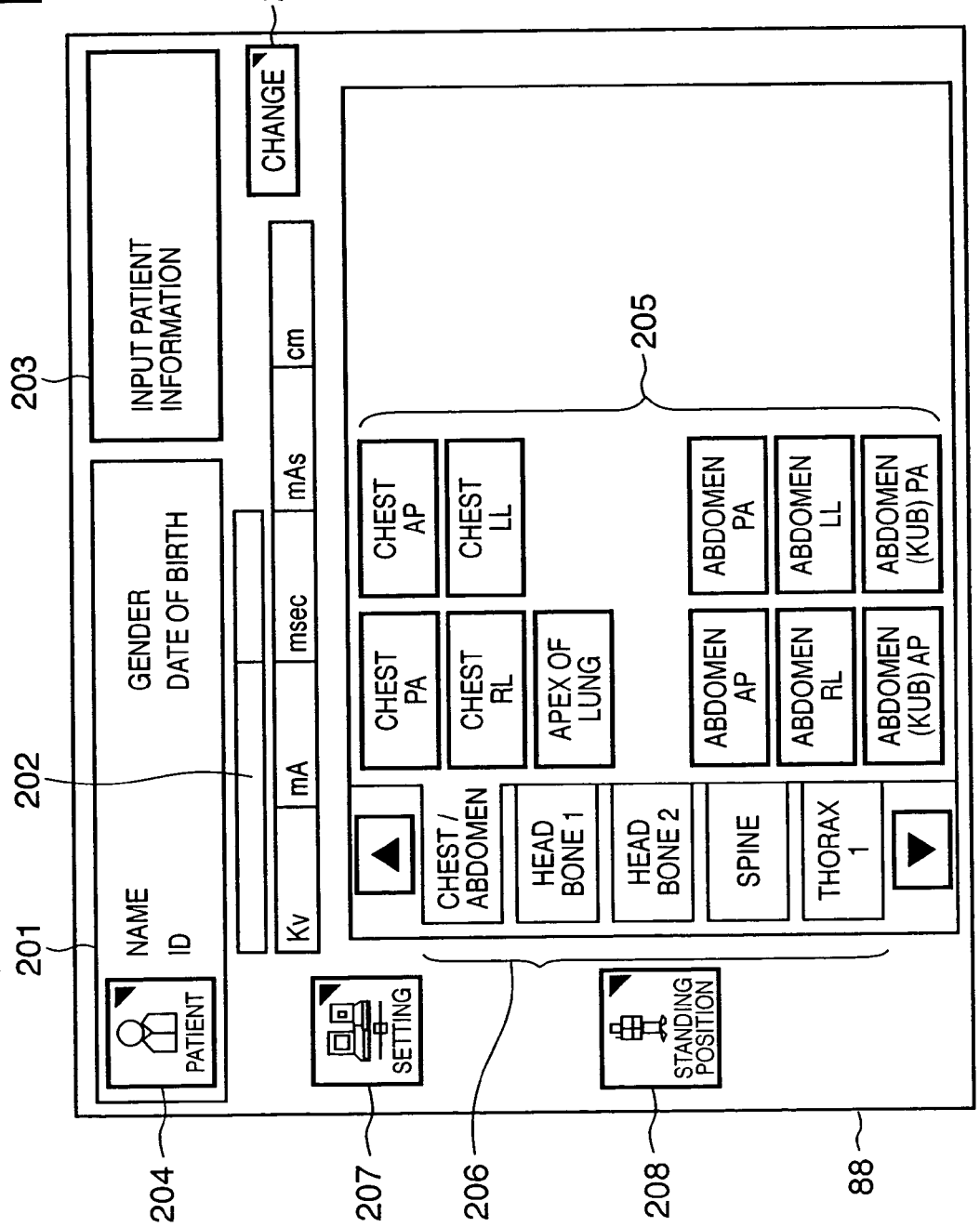
FIG. 2 is a view for explaining an example of a user interface for imaging preparation.

FIG. 2 shows an example of an imaging preparation window displayed on the operation/display unit 88 of the X-ray imaging apparatus. In FIG. 2, a patient information display field 201 displays patient information such as the name, ID, gender, birth date, and the like of a patient. An imaging condition display field 202 displays imaging conditions such as an X-ray tube current, tube voltage, irradiation time, patient-tube distance, and the like. Note that the patient information is input using a patient information input window by clicking a patient information input window call button 204 to display that window.

Note that imaging method select buttons 205 are state maintaining buttons. Once these buttons are pressed, they are displayed in a depressed state until they are canceled, thus indicating the selected imaging methods. The imaging method select buttons 205 are preset with various settings that allow operations on windows shown in FIGS. 5 and 6 (to be described later), i.e., settings of radiographic parameters including settings of valid AEC regions and operation conditions of the X-ray generator, settings of image processing parameters, settings of a correction process, and generator settings such as a stop, focal point size, and the like, in addition to the imaging conditions to portions to be radiographed.

Imaging portion switching tabs 206 are used to switch categories of portions such as chest/abdomen, head, and the like, and a chest/abdomen tab is selected in FIG. 2. A parameter change button 209 is used to call the windows shown in FIGS. 5 and 6 so as to change parameters of the selected imaging method select button 205.

A state/message display field 203 displays messages and a system state. A setting window call button 207 is used to call various setting windows. A sensor select button 208 is used to select a sensor. In this example, only a standing position type sensor is connected. However, when a plurality of sensors such as a standing position type sensor, a recumbent position type sensor, and the like are connected, this button is used to select such sensors. When the sensor is switched using the sensor select button 208, the imaging portion tabs 206 and imaging method select buttons 205 are switched to those corresponding to the selected sensor.

Figure 3:
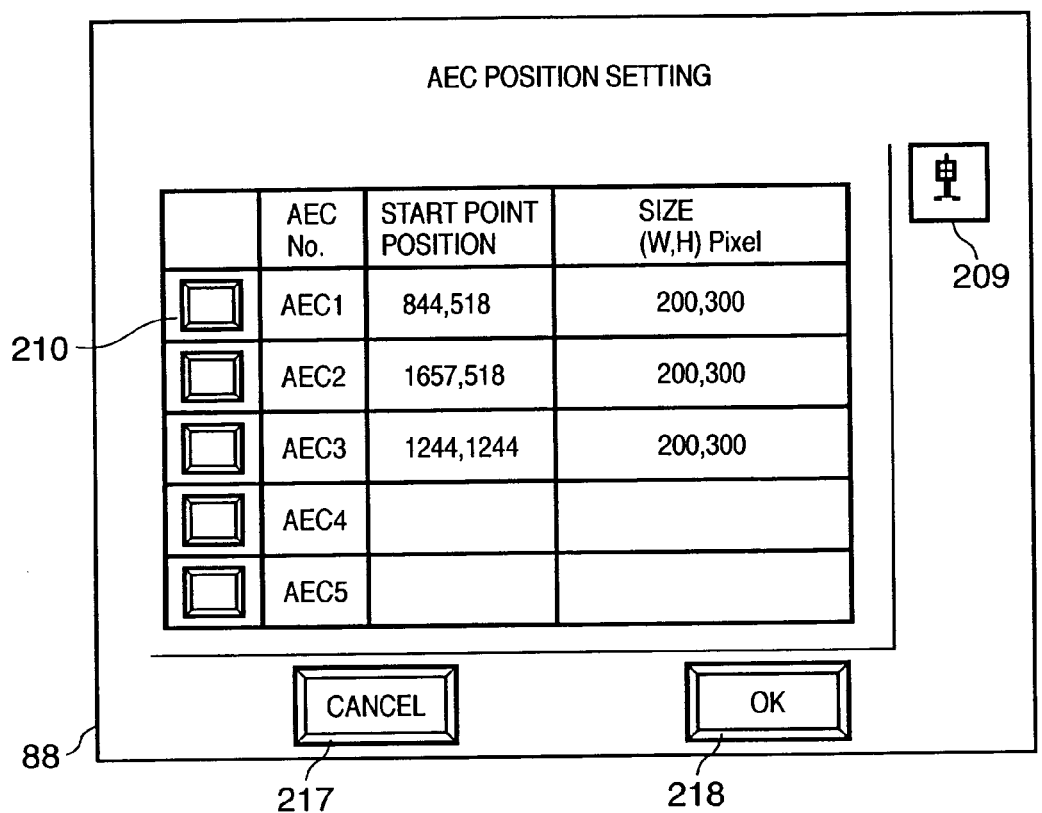
FIG. 3 is a view showing an example of a window used to input the positions and sizes of AEC regions.
Figure 16:
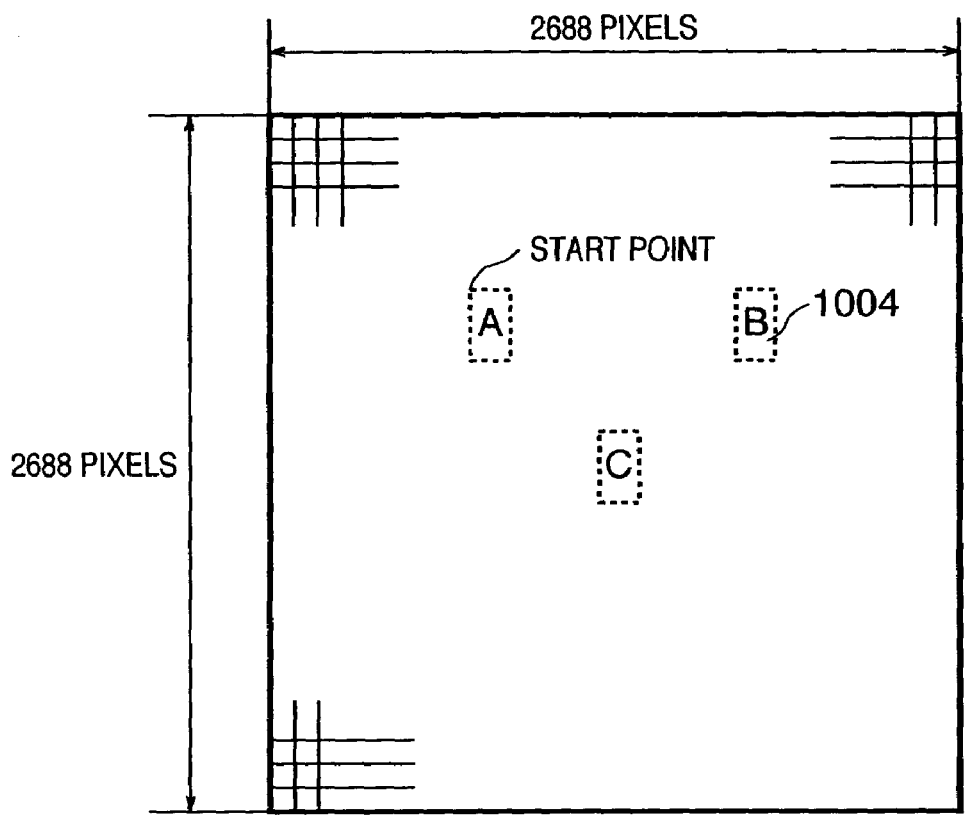
FIG. 16 is a view for explaining the layout of AEC regions.

FIG. 3 shows one of windows called by the setting window call button 207 in FIG. 2, i.e., a window used to set the positions and sizes of AEC regions for each sensor. On this window, a maximum of five AEC regions which are included in the imaging unit 1003 and are laid out can be set and registered. The start point position of each AEC region is designated in units of pixel using a coordinate whose origin is on the upper left point of an effective pixel region of the X-ray detector 1005 (sensor) shown in FIG. 16. More specifically, the start point position of the AEC region is the coordinate of the upper left point of that region on the coordinate system. Also, the size of each AEC region is designated for respective pixels of the X-ray detector 1005. An OK button 218 and cancel button 217 are respectively used to settle settings and to cancel settings.

Figure 4:
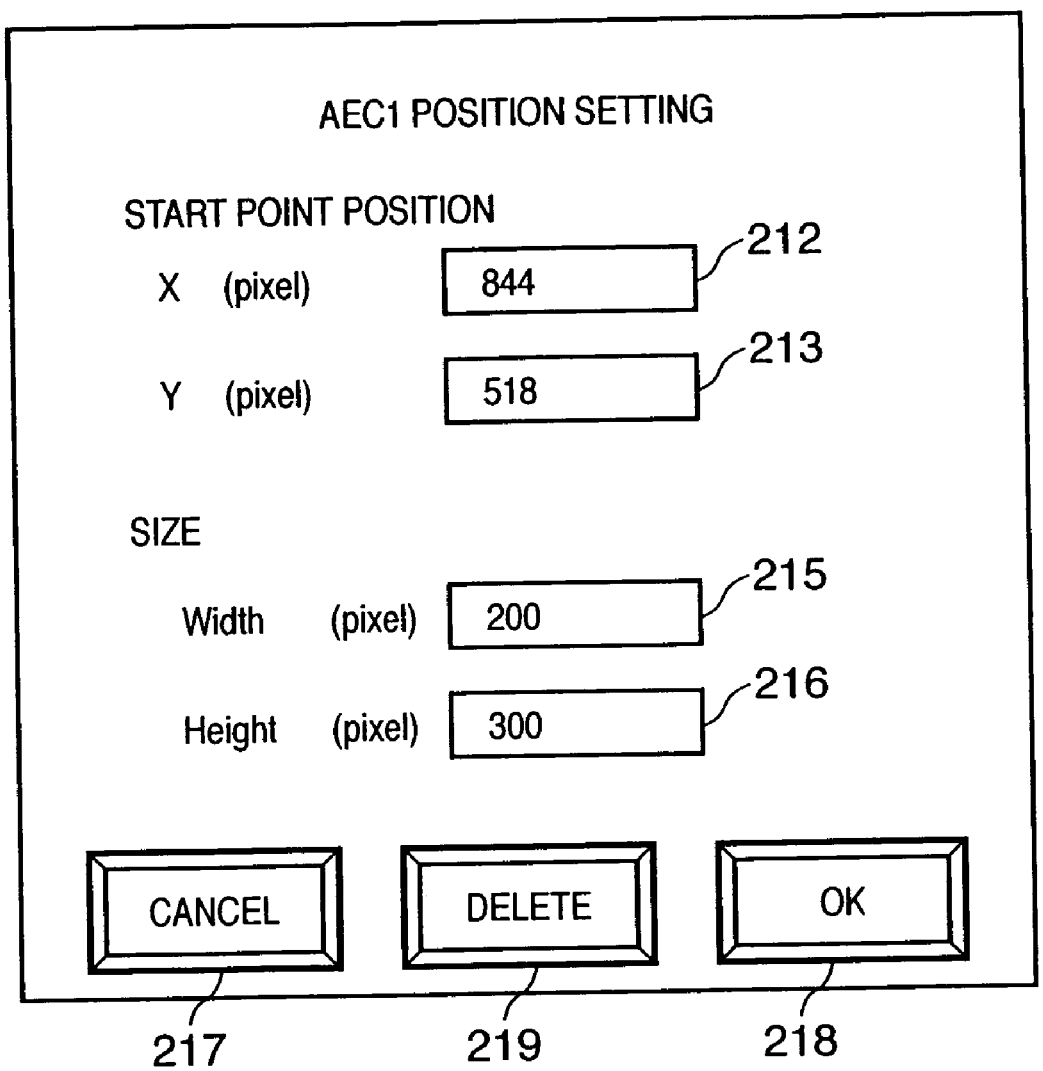
FIG. 4 is a view for explaining a dialog used to set the position and size of an AEC region.

When the start point position and size of each AEC region are to be changed, the following operation is made. When the user clicks an AEC position/size setting button 210 corresponding to a desired AEC number on the setting window in FIG. 3, an AEC position/size setting dialog shown in FIG. 4 is displayed. On the dialog in FIG. 4, the upper left coordinate position (X-coordinate (212), Y-coordinate (213) and the width (215) and height (216) of an AEC valid region are set for respective pixels of the sensor. Reference numerals 212 to 216 denote edit boxes to which numerical values are input directly or using a software ten-key pad. Reference numeral 219 denotes a delete button which is used to delete the coordinate position and size of the set AEC region.

The coordinate positions and sizes of the AEC regions designated using the user interfaces shown in FIGS. 3 and 4 are held on the AEC region table 10, as shown in FIGS. 1 and 7A. For an AEC region whose contents are deleted by the delete button 219, "0"s are input to all position and size fields on the table.

Figure 5:
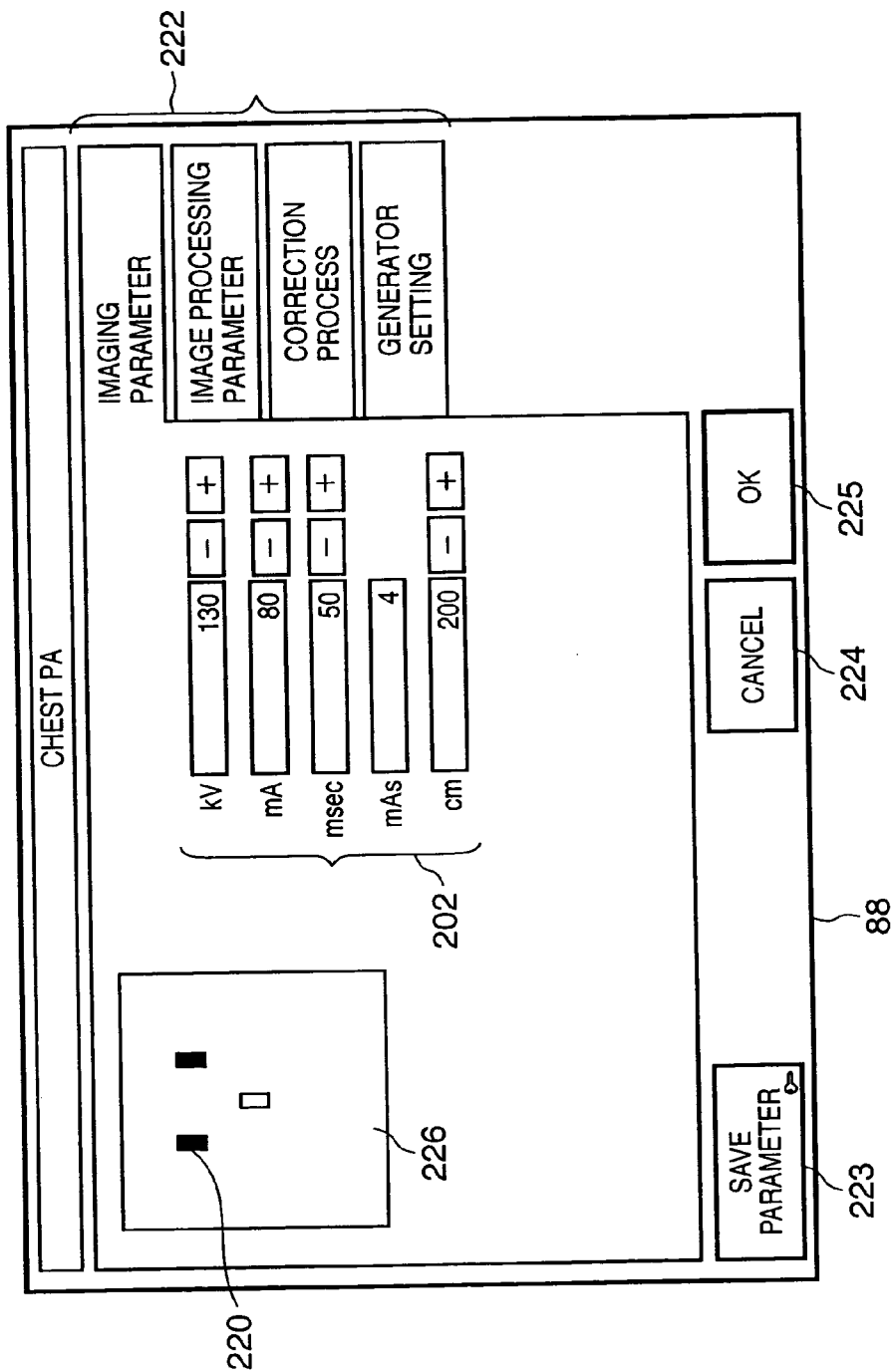
FIG. 5 is a view showing a display example of a parameter change window corresponding to chest PA.
Figure 6:
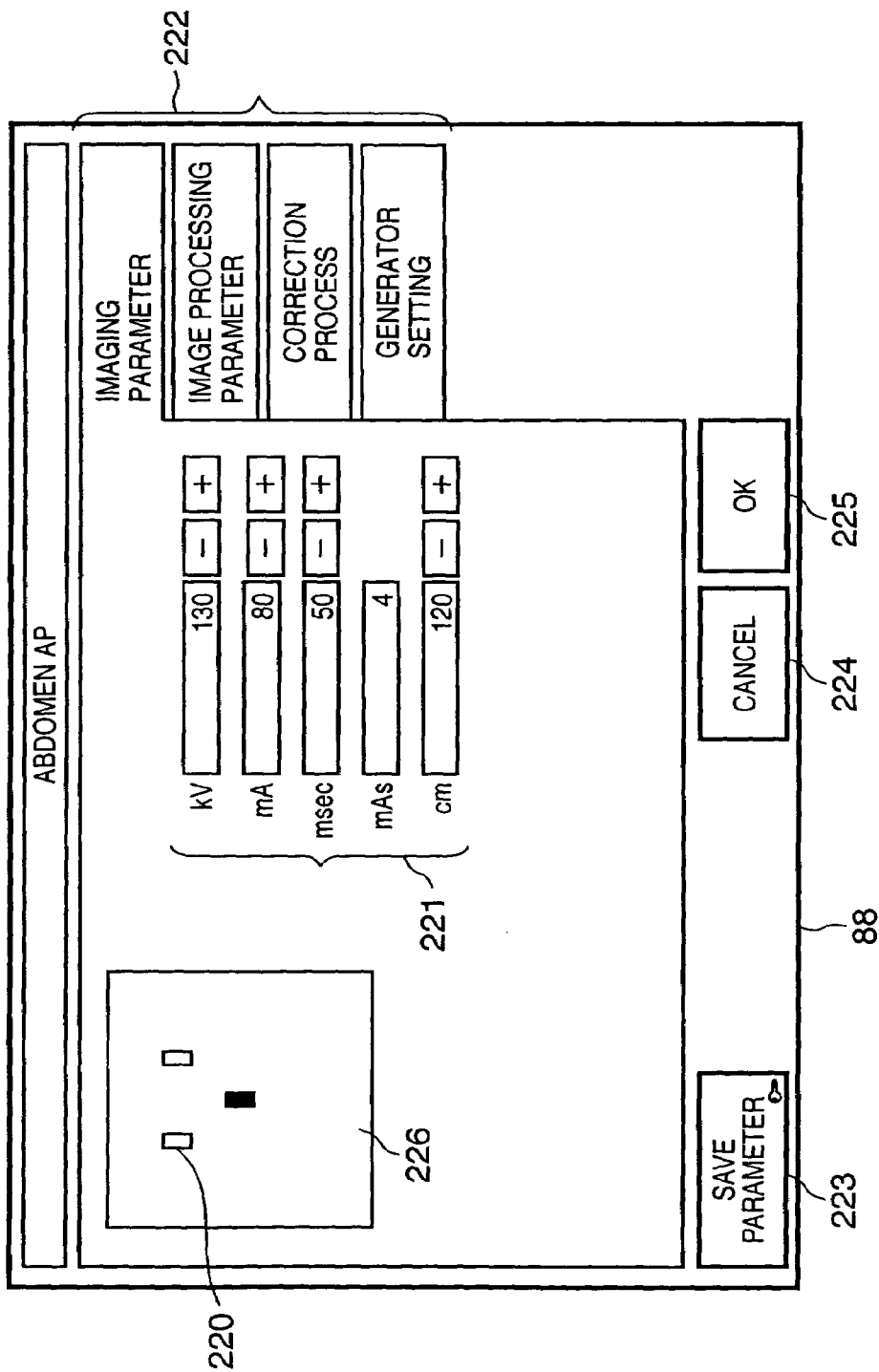
FIG. 6 is a view showing a display example of a parameter change window corresponding to abdomen AP.

FIGS. 5 and 6 show parameter change windows called upon clicking the parameter change button 209 shown in FIG. 2, i.e., parameter change windows respectively called when chest PA and abdomen AP imaging method buttons are selected. AEC select buttons 220 are laid out on a region 226 indicating the effective detection region of the X-ray detector 1005 on the basis of the positions and sizes of the AEC regions which are set for respective AEC regions on the setting window in FIG. 3. Each AEC select button 220 is a state maintaining button, and is kept depressed while a corresponding region is selected. In FIGS. 5 and 6, black rectangles indicate the selected regions. In FIG. 5, since chest imaging is selected, two, upper right and left AEC regions (AEC1, AEC2) are selected to select two lung fields as regions of interest. In the abdomen imaging in FIG. 6, a central AEC region (AEC3) is selected and enabled. Reference numerals 202 (FIG. 5) and 221 (FIG. 6) denote drive conditions of the X-ray generator, which are set in correspondence with the respective imaging methods.

The AEC regions (or region) to be used set for each imaging method using the user interface shown in FIG. 5 or 6 are held in the imaging method-dependent AEC region table 11, as shown in FIGS. 1 and 7B. In FIG. 7B, each AEC region corresponding to an AEC number which is set "On" is the one to be used. The imaging method-dependent AEC region table 11 has an imaging method ID, and can be designated together with the desired imaging method select button 205 on the basis of the imaging method ID sent from HIS (hospital information system), RIS (radiology information system), or the X-ray generator (X-ray generator controller 1002).

Figure 8:
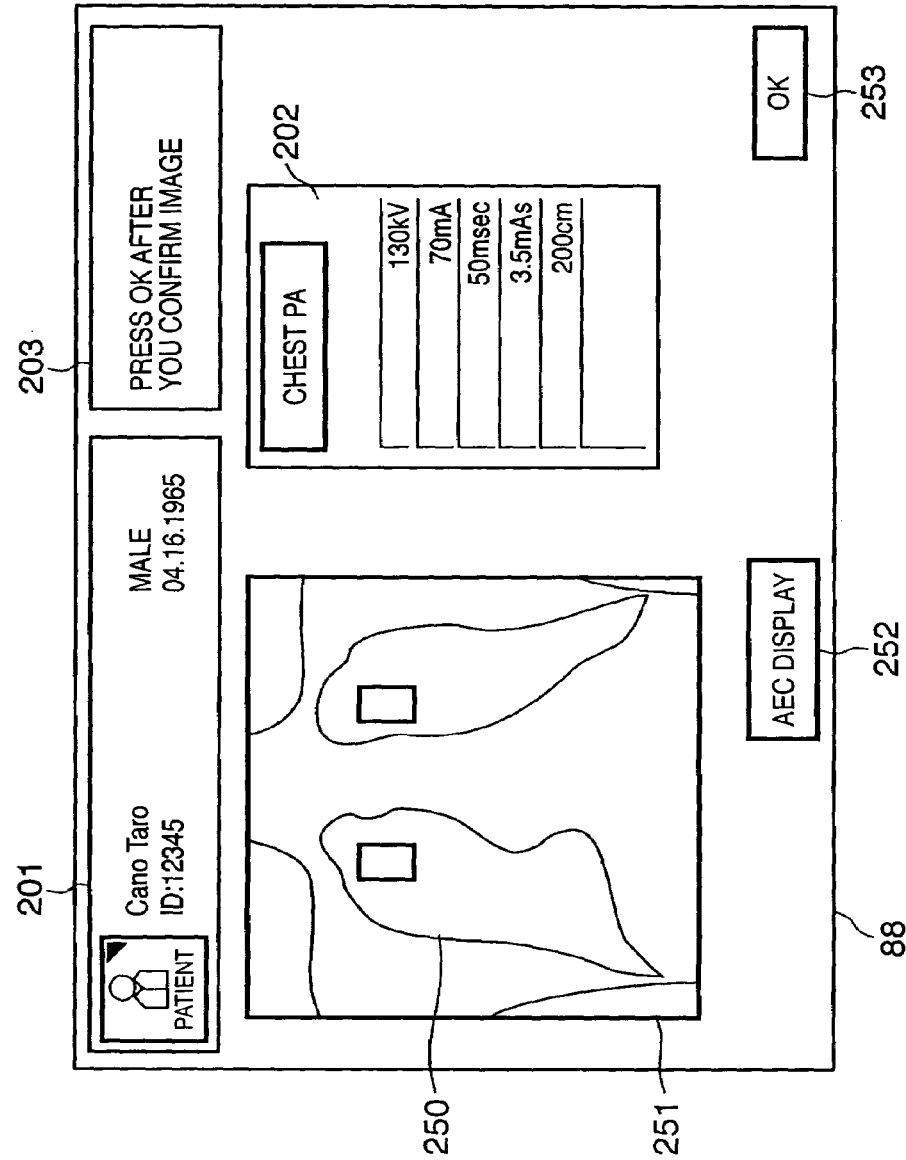
FIG. 8 is a view showing a window display example on a user interface after X-ray imaging.

FIG. 8 shows a state wherein the user clicks an AEC display button 252 after imaging to superimpose valid AEC regions on a radiographic image 251. In this manner, since AEC regions used in imaging are explicitly displayed on the radiographic image, whether or not AEC settings of the operator are good can be easily and quickly determined.

The operation of the imaging system controller 1006 in the X-ray imaging system of this embodiment with the above arrangement will be described in detail below.

A radiological technologist or doctor as an operator (to be referred to as an operator hereinafter) determines patient information and an imaging method using the user interfaces provided by the operation/display unit 88. The patient information is input from the patient information input window called by clicking the patient button 204. Alternatively, in terms of improvement of input operation efficiency and prevention of input errors, the patient information may be input using a magnetic card or barcode (not shown) or may be acquired from the HIS or RIS. The input patient information is displayed on the patient information display field 201.

The operator selects a desired tab by selecting the imaging portion select tabs 206, and then clicks the imaging method select button 205 so as to set a portion to be radiographed. For example, when the operator wants to perform chest PA imaging, he or she clicks the imaging method select button 205 indicating "chest PA". Various parameters indicated by parameter select tabs 222 In FIG. 5, e.g., imaging parameters, image processing parameters, correction process parameters, and generator setting parameters are set for each imaging method as preset values using the user interface shown in FIG. 5. Upon clicking the desired imaging method select button 205, parameters corresponding to that imaging method are acquired. Some of the acquired parameters are displayed on the imaging condition display field 202 in FIG. 2.

Upon clicking the parameter change button 209, the parameter change window shown in FIG. 5 is called. At this time, the AEC select buttons (or button) 220 are displayed in accordance with the positions and sizes of the AEC region table and the selected state of the AEC regions (or region) in the imaging method-dependent AEC region table of chest AP. That is, the positions and sizes of AEC regions are settled based on the AEC region table 10, and AEC regions to be selected are settled based on the imaging method-dependent AEC region table (11) of chest AP.

In case of chest PA, the upper left and right regions are selected to allow the operator to confirm chest imaging. If a patient who has only one lung is to be radiographed, the AEC select button corresponding to an absent lung is changed to OFF. When the parameter has changed, that value is saved in the imaging method-dependent AEC region table 11 shown in FIGS. 7B and 1 upon clicking an OK button 225. The user interface then transits to the window shown in FIG. 2. Upon clicking a cancel button 224 on the window shown in FIG. 5, changes in respective setting values are canceled. Upon clicking a parameter save button 223, the imaging method-dependent AEC region table is changed, and the preset values of the parameters are changed. Then, the window transition is made.

FIG. 6 shows a parameter change window upon clicking an imaging method select button 205 indicating abdomen AP, and its contents are the same as those of the window shown in FIG. 5.

Next, the operator instructs the patient 109 to stand, as shown in FIG. 1, and moves up/down an elevating stage using an elevating stage pedal (not shown) to adjust the position of the patient 109 to an appropriate position with respect to the imaging unit 1003. For example, in "chest PA" imaging, the position of the patient is normally adjusted so that the upper end of the imaging unit 1003 is flush with the shoulders of the patient. The patient-tube distance is changed by moving the X-ray tube 1000 back or forth, and an exposure field stop is adjusted so that only a portion to be radiographed is irradiated with X-rays.

Upon completion of imaging preparation, the image capture controller 81 shown in FIG. 1 applies a voltage to the solid-state imaging element using a solid-state imaging element drive control signal, so as to prepare for a state wherein the solid-state imaging element can receive an image of the patient 109 anytime.

Various preset parameters (imaging parameters, image processing parameters, correction process, and generator setting parameters) called by the imaging method select button 205 and parameters which have been changed on the parameter change window are transferred to the imaging unit 1003, respective modules in the imaging system controller 1006, and X-ray generator controller 1001. The respective units stand by in accordance with the transferred parameters, so that they are ready to radiograph using the designated parameters. In this case, information of the valid AEC regions (or region) is acquired from the imaging method-dependent AEC region table 11 to switch the valid regions (or region) of the AEC device 1004.

The operator then presses an X-ray exposure button (e.g., a switch connected to the console 1002 via a cable having a length of about 1 to 2 m) arranged in the vicinity of the operation/display unit 88 of the X-ray imaging apparatus. This exposure button serves as a trigger for generating X-rays by the X-ray tube 1000. When the operator presses this exposure button, the imaging system controller 1006 generates an exposure signal to the X-ray generator controller 1001. The exposure signal generated upon depression of the button is temporarily supplied to the image capture controller 81. Upon reception of this signal, the image capture controller 81 confirms based on the status of a drive notification signal generated by the solid-state imaging element whether or not the solid-state imaging element (FPD1005) is ready to convert X-rays from the X-ray tube 1000 into an image. After that, the controller 81 generates an exposure permission signal to an exposure switch. This exposure permission signal turns on the exposure permission switch to supply the exposure signal generated by the exposure button to the X-ray generator controller 1001. Note that the exposure signal is generated upon depression of the second switch of the exposure button.

The X-ray generator controller 1001 applies a high voltage to the X-ray tube 1000 in response to the exposure signal to generate X-rays. The exposure conditions at that time are set on the basis of the aforementioned preset values or values obtained by changing these preset values on the parameter change window. The X-ray generator controller 1001 generates X-rays for a time specified by the irradiation time. If the sum total of AEC signals (X-ray dose signals) fetched and integrated by the X-ray generator controller 1001 via the selected regions (or region) of the AEC device 1004 has reached a predetermined amount, the controller 1001 cuts off X-ray generation of the X-ray tube 1000. Normally, the irradiation time given as the exposure conditions is set to be relatively longer upon executing the X-ray dose control using the AEC device 1004. After exposure described above, X-rays generated by the X-ray tube 1000 are stopped down by an exposure field stop, are transmitted through the patient 109, and the grid and scintillator (not shown) in turn, and form an image on the solid-state imaging element as a radiographic image. By photoelectric conversion of the solid-state imaging element, the image is output as an image signal. This image signal is converted into a digital signal by the A/D converter, and the digital signal is captured by the image capture controller 81.

The X-ray image obtained by the aforementioned imaging operation is converted into a digital signal, which is captured by the imaging system controller 1006 via the image capture controller 81. The captured image undergoes various correction processes and image processes by the image processor 82. The image undergoes image correction such as correction of variations of photoelectric conversion elements that form the sensor, correction of aging of sensor elements, scattered ray correction, grid correction, and the like. The corrected image information then undergoes analysis for extracting a region of interest and extracting the exposure field and a non-object region of X-rays. For example, when the radiographic image is "chest front", a region of the lung fields is extracted. An image is extracted into a desired size based on the extracted exposure field region data, and is converted based on a desired density characteristic curve, thus creating an image with desired halftone characteristics.

The created image is displayed as a radiographic image 251 on a given field of the operation/display unit 88 of the X-ray imaging apparatus, as shown in FIG. 8. The operator checks by observing the radiographic image 251 if the image is not blurred, graininess has an appropriate level, the patient posture is correct, and so forth. Furthermore, the operator confirms if the contrast and density are appropriate. After that, the operator presses an imaging end key to end imaging.

Normally, when the radiographic image does not have a diagnosis level, the image quality is improved by applying image processes such as dynamic range compression, sharpening process, and the like. However, when the X-ray dose of the region of interest does not reach a predetermined amount, the image graininess is significant, and the image cannot have a diagnosis level even after any image processes. In this case, the operator must suspect if the dose control based on AEC is normally working. However, in the conventional mechanism, the operator cannot recognize it instantly.

In the X-ray imaging system of this embodiment, when the image quality is low (e.g., significant graininess), the operator presses the AEC display button 252. Upon depression of the AEC display button 252, the AEC region display unit 83 in FIG. 1 acquires the AEC regions (or region) which are set to be valid for the imaging method of interest from the imaging method-dependent AEC region table 11, and acquires the coordinate positions and sizes of these valid AEC regions from the AEC region table 10. The unit 83 superimposes the valid AEC regions 250 on the radiographic image 251 on the basis of the acquired coordinate positions and sizes of the valid AEC regions, as shown in FIG. 8.

Note that the AEC display button 252 is a state maintaining button that maintains an ON or OFF state. Immediately after imaging, the button 252 is OFF and no AEC regions are displayed. When the operator turns on the AEC display button 252 (its display is switched to a depressed state), the valid AEC regions 250 are displayed, as shown in FIG. 8. As is obvious at a glance from FIG. 8, since the AEC regions are superimposed, the operator can check if each AEC region matches the region of interest, if AEC region choice is correct, and so forth. Hence, the operator can instantly determine if imaging is to be redone, and can easily make AEC selection and positioning correction, thus preventing repetition of identical errors. That is, if the valid AEC regions are wrong, the operator can re-select correct AEC regions, or if the region of interest deviates from each AEC region, the operator can re-position the patient, thus obtaining a radiographic image with high image quality. Especially, in case of chest side imaging, individual differences are large, and it is difficult to determine the position of interest of a spine from outside due to a different body thickness. Hence, with the conventional system, the operator cannot immediately determine causes of poor image quality, but he or she can easily determine them according to this embodiment.

Note that the valid AEC regions 250 are required to be displayed only when the image quality is poor, but are troublesome if they are displayed all the time. Hence, this embodiment does not normally display AEC regions but displays them only when the AEC display button 252 is pressed. When the operator makes adjustment operations of image processing parameters and the like or when the window transition takes place, the AEC display button 252 is automatically switched from ON to OFF to execute a process for aborting display of the AEC regions, thus effectively improving the operability.

When the operator quits imaging by pressing an OK button 253, the position and size information of the AEC regions used and the information of the valid AEC regions are saved in the storage 84 connected via the network 110 together with text information such as patient information, imaging information, image processing parameters, and the like, and the X-ray radiographic image. For this reason, even after imaging, this image can be read out from the storage 84 and the AEC regions used can be displayed.

The X-ray imaging operation according to the first embodiment will be described below with reference to the flowchart of FIG. 9.

The aforementioned user interface provided by the operation/display unit 88 is presented to a user, and the control prompts the user to input patient information and an imaging method (steps S1 and S2). At this time, the position information and size information of AEC regions to be used are acquired from the AEC region table 10 (FIG. 7A). In step S4, information of AEC regions to be validated is acquired from the imaging method-dependent AEC region table 11 (FIG. 7B) on the basis of the imaging method designated via the user interface.

X-ray exposure is executed in response to an instruction input by the operator, and the imaging unit 1003 acquires an X-ray image (step S5). In step S6, the image capture controller 81 captures an X-ray radiographic image from the imaging unit 1003, the image processor 82 applies various image processes, and a radiographic image is displayed on the operation/display unit 88 based on the processed image data. If it is determined in step S7 that the AEC display button is pressed, the flow advances to step S8 to superimpose the valid AEC regions acquired in step S4 of those to be used acquired in step S3 on the radiographic image in accordance with the coordinate positions and sizes registered in the table 10. It is checked in step S9 if the OK button 253 is pressed. If the OK button 253 is pressed, the flow advances to step S10 to save the position and size information of the AEC regions used and the information of the valid AEC regions in the storage 84 together with the imaging image. If it is determined in step S7 that the AEC display button is not pressed, the control skips step S8. On the other hand, if it is determined in step S9 that the OK button 253 is not pressed, the flow returns to step S7.

In this embodiment, only the standing position type sensor is connected, but a recumbent position type sensor may be connected at the same time. In this case, the positions and sizes of the AEC regions for the recumbent position type sensor can be set by switching the sensors using the sensor select button 208 in FIG. 3.

In the first embodiment, the patient information and portion to be radiographed are manually input and selected. Alternatively such information may be input from an external information system such as the HIS, RIS, X-ray generator, and the like. In this case, the imaging method ID that indicates selection of the portion to be radiographed and the imaging method is designated from the external information system. Or a table that associates processing IDs and imaging method IDs may be prepared, and the imaging method ID corresponding to the externally input processing ID may be specified to set the imaging method.

Second Embodiment

The second embodiment will explain a case wherein patient information and AEC region information are transferred from the HIS, RIS, and X-ray generator (X-ray generator controller 1002).

FIGS. 10A and 10B partially show imaging request information transferred from the HIS, RIS, and generator. FIG. 10A shows patient information and imaging portion information transferred from the HIS or RIS before X-ray exposure. FIG. 10B shows execution information sent from the generator after X-ray exposure. Note that the execution information in FIG. 10B may be received via the HIS or RIS in place of being directly received from the generator.

A case will be explained first with reference to the flowchart of FIG. 11 wherein patient information and imaging method information (including a portion to be radiographed, imaging direction, and the like) are received from the HIS or RIS, and AEC regions (or region) are settled using these pieces of information before X-ray exposure (before imaging). A case will next be explained with reference to the flowchart of FIG. 12 wherein information associated with the AEC regions (or region) is received and the AEC regions (or region) are settled after X-ray exposure (after imaging).

Figure 11:
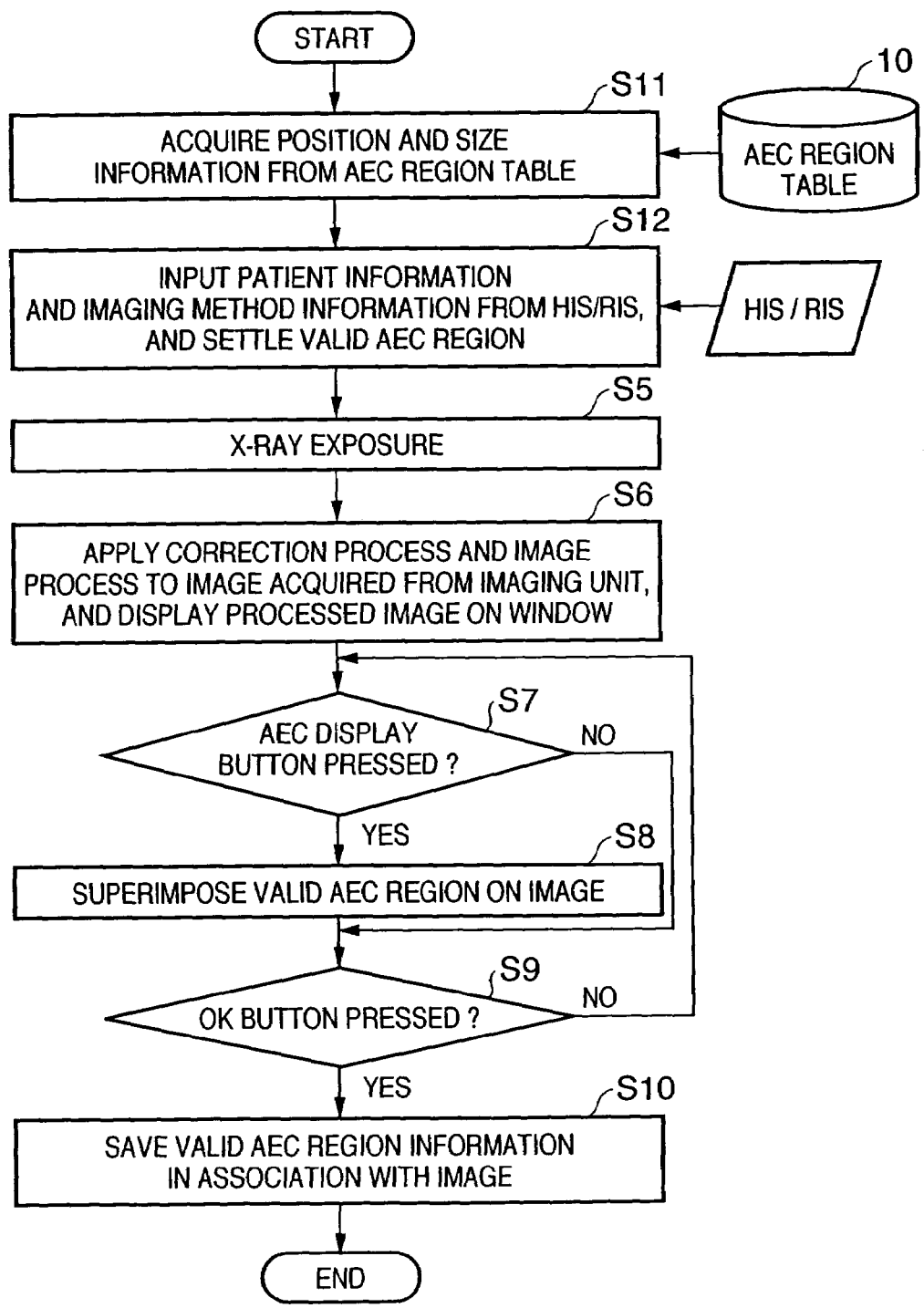
FIG. 11 is a flowchart for explaining the processing sequence of an imaging system controller according to the second embodiment.

As shown in FIG. 11, the positions and sizes of available AEC regions are acquired with reference to the AEC region table 10 in step S11. In step S12, patient information and imaging method information are acquired from the imaging request information in a format shown in FIG. 10A transferred from the HIS or RIS. Based on the imaging method information, X-ray exposure conditions are set. As shown in FIG. 10A, since the imaging method information describes information of valid AEC regions, this information is held in the memory.

After that, processes from execution of X-ray imaging in step S5 until a radiographic image is saved in step S10 are substantially the same as those described in the first embodiment (FIG. 9). Note that the information of the valid AEC regions used in steps S8 and S10 are obtained by reading out that saved in the memory in step S12.

Figure 12:
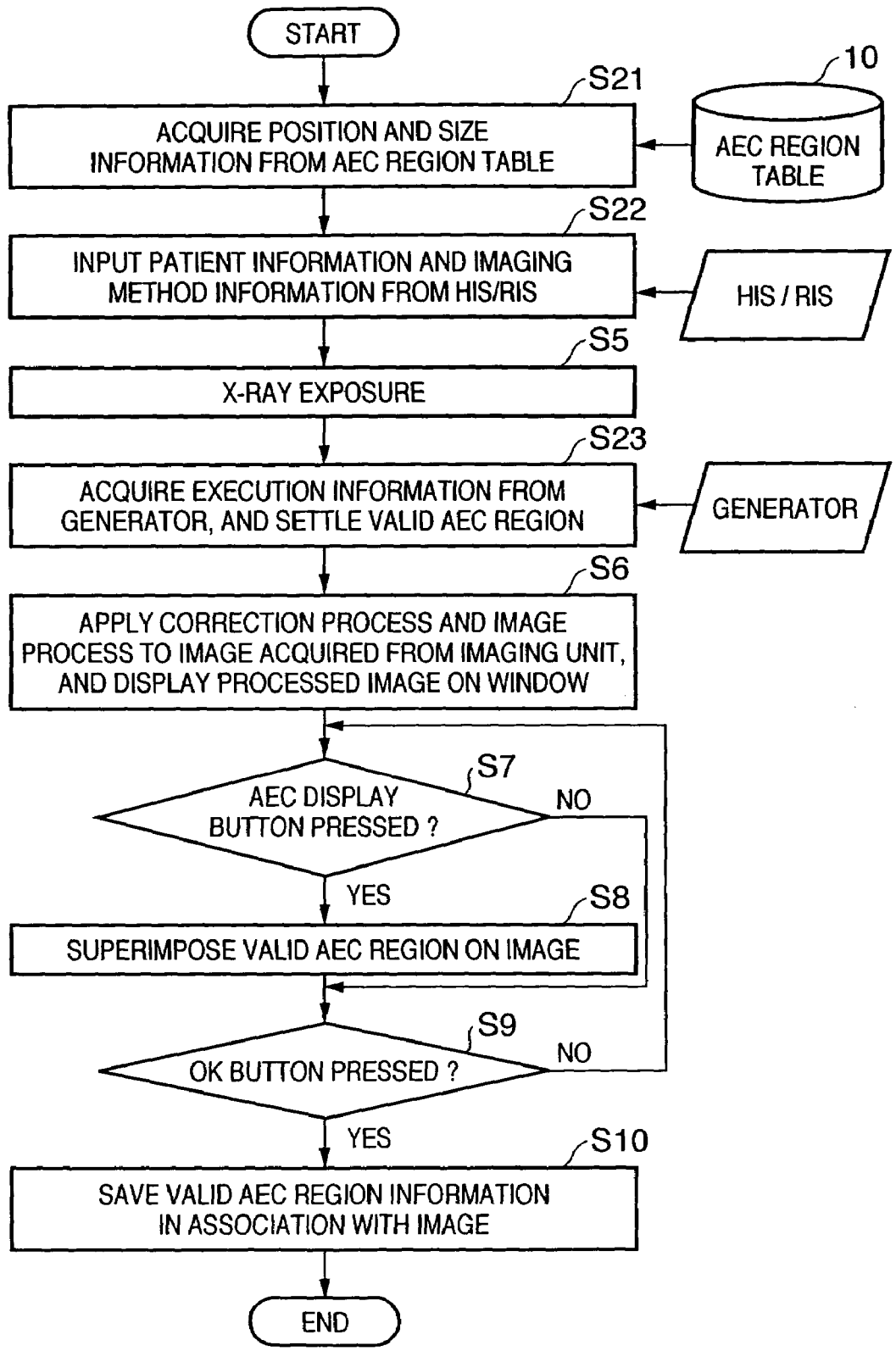
FIG. 12 is a flowchart for explaining the processing sequence of an imaging system controller according to the second embodiment.

As shown in FIG. 12, the AEC regions can be displayed on the basis of the execution information from the generator. In step S21, the positions and sizes of available AEC regions are acquired with reference to the AEC region table 10. In step S22, patient information and imaging method information are acquired from the imaging request information in a format shown in FIG. 10A transferred from the HIS or RIS, and are stored in the memory. Based on the imaging method information, X-ray exposure conditions are set. At this time, even when the imaging method information from the HIS or RIS include the information of AEC regions, it need not be held.

After execution of X-ray imaging in step S5, execution information indicating the execution state of X-ray imaging is acquired from the generator in a format shown in FIG. 10B in step S23. As shown in FIG. 10B, since the execution information describes the information of valid AEC regions, this information is held in the memory. After that, the processes in steps S6 to S10 are the same as those in the first embodiment (FIG. 9). Note that the information of valid AEC regions used in steps S8 and S10 uses that saved in the memory in step S23.

As described above, according to the second embodiment, since valid AEC regions are acquired from the HIS or RIS, or valid AEC region information is directly or indirectly acquired from the execution information of the generator, the imaging method-dependent AEC region table need not be generated unlike in the first embodiment. That is, the imaging system controller 1006 can acquire valid AEC regions for imaging from the imaging request information acquired from the HIS or RIS or the execution information which is acquired from the generator and includes AEC region information actually used in imaging, and can superimpose the AEC regions on a radiographic image.

As described above, according to the second embodiment, since the imaging method-dependent AEC region table need not be generated, the number of operation steps can be reduced. When the execution information from the generator is used, AEC regions actually used in imaging can be acquired more reliably.

Third Embodiment

In the first and second embodiments described above, the operator presses the AEC display button 252 after imaging to superimpose valid AEC regions on a radiographic image. In the third embodiment, the validity of AEC regions is checked on the basis of image data, and if it is determined that AEC region settings obviously have a problem, AEC regions are automatically superimposed on a radiographic image. For example, when the average pixel value of each valid AEC region is apparently different from that in the AEC region in a normal imaging state, that AEC region is more likely to be incorrect. Hence, valid AEC regions are preferably displayed for the operator without waiting for depression of the AEC display button 252 by the operator.

Figure 13:
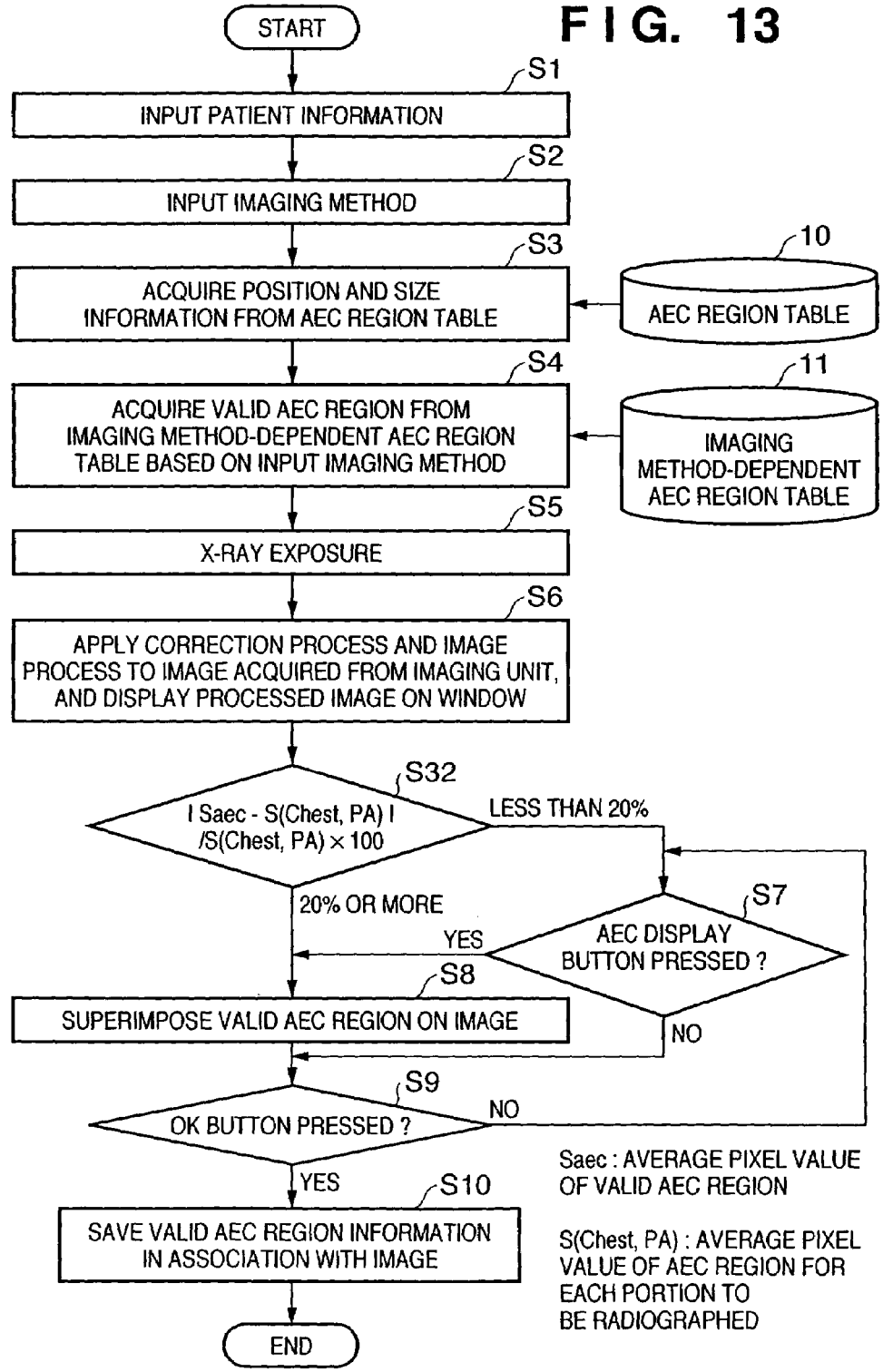
FIG. 13 is a flowchart for explaining the processing sequence of an imaging system controller according to the third embodiment.

FIG. 13 is a flowchart for explaining the process of the imaging system controller 1006 according to the third embodiment. Steps S1 to S6 are the same as those in the first embodiment. Of course, the processes up to step S6 may be replaced by those (steps S11, S12, S5, and S6 in FIG. 12 or steps S21, S22, S5, S23, and S6 in FIG. 13) described in the second embodiment.

After an X-ray radiographic image is displayed on the operation/display unit 88 in step S6, it is checked in step S32 based on the X-ray radiographic image if AEC regions (or region) are to be displayed. Since AEC regions to be used and their average pixel values are different depending on portions to be radiographed, a table that registers AEC region average pixel values for respective portions to be radiographed is prepared. Also, even when the portion to be radiographed remains the same, the average pixel value varies depending on imaging directions, and is as a function of a direction. That is, an AEC region average pixel value S is a function of (imaging portion, imaging direction). For example, in chest PA imaging, since the portion to be radiographed is Chest, and the imaging direction is PA, the AEC region average pixel value in chest PA imaging is expressed by S(chest, PA). Let Saec (obtained by extracting an AEC region from imaging data and calculating a pixel average) be the average value for each valid AEC region in this imaging. Then, an error is given by:

$$|Saec-S(chest, PA)|/S(chest, PA) \times 100 \qquad (1)$$

Note that the AEC region average pixel value is calculated by dividing the sum total of pixel values in the AEC region by the number of pixels.

If the calculation result of formula (1) indicates an error of 20% or more, it is determined that incorrect AEC regions (or region) are selected or each valid AEC region does not match the region of interest. Hence, the flow advances to step S8 to superimpose valid AEC regions on a radiographic image as in the first embodiment. After that, upon depression of the OK button, the valid AEC region information and radiographic image are saved in association with each other as in the first and second embodiments. If it is determined in step S32 that the calculation result of formula (1) indicates less than 20%, since it is determined that correct AEC regions (or region) are selected, and each valid AEC region matches the region of interest, the valid AEC regions are not superimposed until an AEC display instruction is input by the operator (step S7). Note that the average pixel value in each AEC region is used in the above description. Alternatively, the average pixel value in a region of interest (ROI) extracted from the radiographic image may be used. In this case as well, standard average pixel values of regions of interest corresponding to the imaging methods are held as reference values, the average pixel value is calculated for a region of interest extracted from the imaging data and is compared with the held reference value (corresponding to the imaging method of that radiographic data), and it is checked if an error is 20% or less. If a plurality of AEC regions are set, the average values of all AEC regions are used. Of course, the average pixel value of each individual AEC region may be used.

Figure 14:
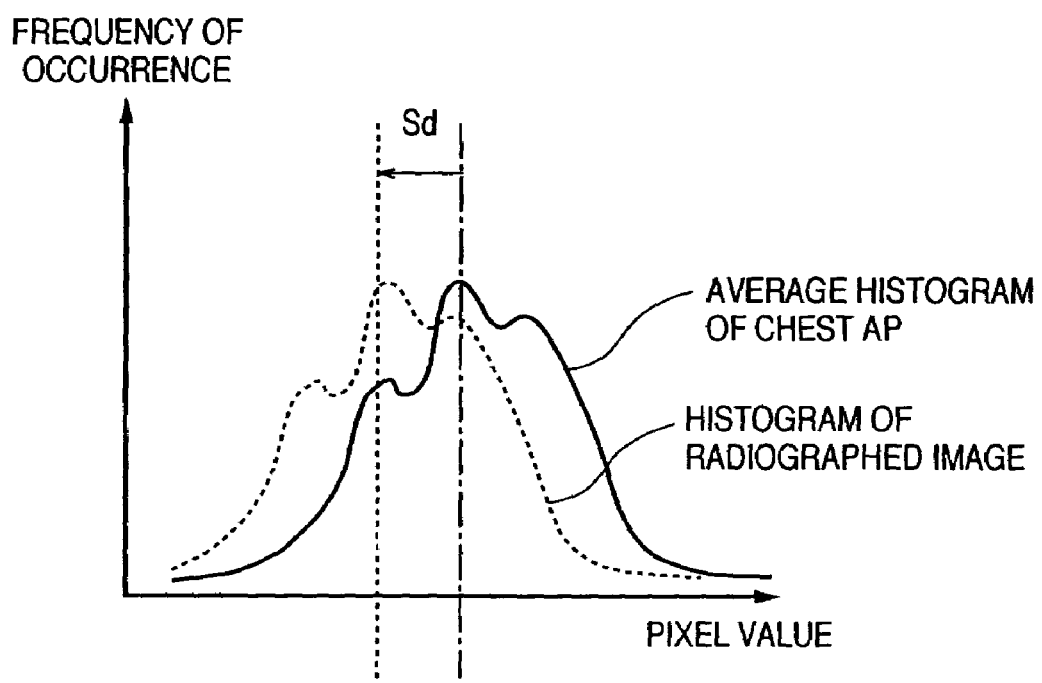
FIG. 14 is a view for explaining a determination example using a histogram so as to determine necessity/unnecessity of AEC region display.

In the third embodiment, the average pixel value in each AEC region is checked upon determining in step S32 if superimposed display of AEC regions is to be executed. However, the present invention is not limited to this. For example, FIG. 14 shows an example of determining using the histogram of the entire radiographic image if correct AEC regions (or region) are selected and each valid AEC region matches the region of interest. The histogram is a frequency distribution curve, and forms a nearly similar shape depending on a portion to be radiographed. By comparing the peak values of frequencies of occurrence, the image quality of the radiographic image can be roughly checked. As the histogram to be used, a histogram of pixel values obtained after image data is captured by the image capture controller 81 and undergoes correction processes such as correction of variations of photoelectric conversion elements that form the sensor, correction of aging of sensor elements, shading, and the like, or a histogram of densities immediately after pixel values are converted into density values using an LUT for each individual portion to be radiographed may be used. That is, histogram comparison is made without density conversion due to translation of an LUT required to adjust densities.

The average histograms of respective portions to be radiographed are held, and a pixel value at a peak of that average histogram is compared with that at a peak of the histogram of a radiographic image, and if a difference Sd between these pixel values is larger than a threshold value S(chest, PA), it is determined that incorrect AEC regions (or region) are selected, or each valid AEC region does not match the region of interest. Note that the threshold value S is expressed as a function S(chest, PA) of the portion to be radiographed and imaging direction, as described above.

As described above, if it is determined that incorrect AEC regions (or region) are selected, or each valid AEC region does not match the region of interest, since AEC regions are automatically superimposed on a radiographic image, the operator need not press the AEC display button 252, and the operationality efficiently advances.

As described above, according to the above embodiments, since the positions of valid AEC regions are superimposed on an image after imaging, when an appropriate X-ray dose cannot be obtained due to selection errors of AEC regions or deviations of AEC regions from regions of interest, its cause can be easily recognized, and an image with an appropriate X-ray dose can be re-radiographed quickly.

Other Embodiments

Note that the present invention is also achieved by supplying a recording medium, which records a program code of a software program that can implement the functions of the above-mentioned embodiments to the system or apparatus, and reading out and executing the program code stored in the recording medium by a CPU of the system or apparatus. In this case, the program code itself read out from the recording medium implements the functions of the above-mentioned embodiments, and the recording medium which stores the program code constitutes the present invention.

As the storage medium for supplying a control program, for example, a flexible disk, hard disk, optical disk, magneto-optical disk, CD-ROM, CD-R, magnetic tape, nonvolatile memory card, EPROM, and the like may be used in addition to the control program RAM.

The functions of the above-mentioned embodiments may be implemented not only by executing the readout program code by the computer but also by some or all of actual processing operations executed by an OS (operating system) running on the computer on the basis of an instruction of the program code.

Furthermore, the functions of the above-mentioned embodiments may be implemented by some or all of actual processing operations executed by a CPU or the like arranged in a function extension board or a function extension unit, which is inserted in or connected to the computer, after the program code read out from the recording medium is written in a memory of the extension board or unit.

Note that the present invention can also be applied to a case wherein a program is distributed to a requestor via a communication line such as the Internet or the like from a storage medium that records a program code of software which implements the functions of the aforementioned embodiments.

As many apparently widely different embodiments of the present invention can be made without departing from the spirit and scope thereof, it is to be understood that the invention is not limited to the specific embodiments thereof except as defined in the appended claims.

CLAIM OF PRIORITY

This application claims priority from Japanese Patent Application No. 2004-024588 filed Jan. 30, 2004, which is hereby incorporated by reference herein.

What is claimed is:

1. A display control apparatus for radiographic data obtained from a radiographic imaging apparatus, comprising:
   a first acquisition unit configured to acquire radiographic data obtained from a radiographic imaging apparatus which controls a radiation dose upon radiographic imaging by detecting a radiation dose in one or a plurality of detection regions;
   a first display control unit configured to control a display of a radiographic image on the basis of the radiographic data acquired by said first acquisition unit;
   a second acquisition unit configured to acquire detection region information indicating a position and range of each detection region used in the radiographic imaging apparatus upon generating the radiographic data; and
   a second display control unit configured to superimpose an image indicating each detection region on the radiographic image displayed by said first display control unit on the basis of the detection region information acquired by said second acquisition unit.

2. The apparatus according to claim 1, further comprising:
   a first table which registers positions and ranges of the one or plurality of detection regions;
   a second table which registers a detection region and/or a combination thereof in correspondence with an imaging method; and
   a holding unit configured to hold designation information that designates an imaging method in association with the radiographic imaging prior to acquisition of the radiographic data, and
   wherein said second acquisition unit specifies each detection region used in the radiographic imaging on the basis of the designation information held in said holding unit with reference to said second table, and acquires the detection region information corresponding to the specified detection region with reference to said first table.

3. The apparatus according to claim 2, further comprising:
   a user interface used to designate an imaging method, and wherein said holding unit holds the imaging method set via said user interface as the designation information.

4. The apparatus according to claim 2, further comprising:
a connection unit configured to connect to a network used to transfer medical information, and
wherein said holding unit externally acquires the designation information via the network.

5. The apparatus according to claim 1, further comprising:
a table which registers positions and ranges of the one or plurality of detection regions; and
a reception unit configured to receive use information which is to be used or was used in the radiographic imaging, and
wherein said second acquisition unit acquires the detection region information with reference to said table on the basis of the use information received by said reception unit.

6. The apparatus according to claim 5, wherein said reception unit receives the use information indicating each detection region used in the radiographic imaging by the radiographic imaging apparatus.

7. The apparatus according to claim 1, further comprising a determination unit configured to determine based on the radiographic data whether or not said second display control unit executes superimpose display on the basis of the radiographic image data.

8. The apparatus according to claim 7, wherein said determination unit compares an average pixel value in the detection region with a reference value which is determined in advance as a standard average pixel value in a detection region corresponding to the imaging method, and determines in accordance with the comparison result whether or not the superimpose display is to be executed.

9. The apparatus according to claim 7, wherein said determination unit compares an average pixel value in a region of interest of the radiographic data, and a reference value which is determined in advance as a standard average pixel value in a region of interest corresponding to the imaging method, and determines in accordance with the comparison result whether or not the superimpose display is to be executed.

10. The apparatus according to claim 7, wherein said determination unit compares a peak pixel value of a density histogram of the entire radiographic data, and a reference value which is determined in advance as a peak pixel value in a density histogram of radiographic data corresponding to the imaging method, and determines in accordance with the comparison result whether or not the superimpose display is to be executed.

11. A display control method for radiographic data obtained from a radiographic imaging apparatus, said method comprising:
a first acquisition step of acquiring radiographic data obtained from an X-ray imaging apparatus which controls an X-ray dose upon X-ray imaging by detecting an X-ray dose in one or a plurality of detection regions;
a first display step of displaying a radiographic image on the basis of the radiographic data acquired in the first acquisition step;
a second acquisition step of acquiring detection region information indicating a position and range of each detection region used in the X-ray imaging apparatus upon generating the radiographic data; and
a second display step of superimposing an image indicating each detection region on the radiographic image displayed in the first display step on the basis of the detection region information acquired in the second acquisition step.

12. A storage medium storing a control program for making a computer execute an X-ray imaging control method of claim 11.

13. An X-ray imaging system including an X-ray imaging unit and a control unit for controlling the X-ray imaging unit, comprising:
a first acquisition unit configured to acquire radiographic data obtained from the X-ray imaging unit which controls an X-ray dose upon X-ray imaging by detecting an X-ray dose in one or a plurality of detection regions;
a transmission unit configured to transmit the radiographic data to the control unit;
a first display control unit configured to control a display of a radiographic image on the basis of the radiographic data transmitted from said transmission unit;
a second acquisition unit configured to acquire detection region information indicating a position and range of each detection region used in the X-ray imaging unit upon generating the radiographic data; and
a second display control unit configured to superimpose an image indicating each detection region on the radiographic image displayed by said first display control unit on the basis of the detection region information acquired by said second acquisition unit.

* * * * *